United States Patent
Lund et al.

(10) Patent No.: US 9,908,860 B2
(45) Date of Patent: Mar. 6, 2018

(54) EPOXIDATION USING PEROXYGENASE

(71) Applicant: Novozymes A/S, Bagsvaerd (DK)

(72) Inventors: Henrik Lund, Vaerloese (DK); Lisbeth Kalum, Vaerloese (DK); Martin Hofrichter, Dresden (DE); Sebastian Peter, Zittau (DE)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/497,548

(22) Filed: Apr. 26, 2017

(65) Prior Publication Data

US 2017/0233355 A1 Aug. 17, 2017

Related U.S. Application Data

(62) Division of application No. 15/250,290, filed on Aug. 29, 2016, now Pat. No. 9,663,806, which is a division of application No. 14/382,957, filed as application No. PCT/EP2013/056326 on Mar. 25, 2013, now Pat. No. 9,458,478.

(60) Provisional application No. 61/622,686, filed on Apr. 11, 2012, provisional application No. 61/636,956, filed on Apr. 23, 2012.

(30) Foreign Application Priority Data

Mar. 31, 2012 (EP) ..................... 12162791
Apr. 23, 2012 (EP) ..................... 12165214

(51) Int. Cl.
| | | |
|---|---|---|
| C07D 301/03 | (2006.01) | |
| C12N 9/00 | (2006.01) | |
| C12P 17/02 | (2006.01) | |
| C12N 9/08 | (2006.01) | |

(52) U.S. Cl.
CPC ......... *C07D 301/03* (2013.01); *C12N 9/0065* (2013.01); *C12P 17/02* (2013.01); *C12Y 111/02001* (2013.01)

(58) Field of Classification Search
CPC .................................................. C07D 301/03
See application file for complete search history.

(56) References Cited

U.S. PATENT DOCUMENTS

| | | |
|---|---|---|
| 6,485,949 B1 | 11/2002 | Piazza et al. |
| 6,605,430 B1 | 8/2003 | Affholter |
| 2013/0017584 A1* | 1/2013 | Hofrichter ............... C12P 7/04 435/146 |
| 2014/0234917 A1 | 8/2014 | Lund et al. |
| 2015/0361456 A1* | 12/2015 | Hofrichter ............... C12P 7/04 435/146 |

FOREIGN PATENT DOCUMENTS

| | | |
|---|---|---|
| DE | 103 32 065 A1 | 1/2005 |
| WO | 2006/034702 A1 | 4/2006 |
| WO | 2008/036061 A2 | 3/2008 |
| WO | 2008/119780 A2 | 10/2008 |
| WO | 2011/120938 A2 | 10/2011 |
| WO | 2012/068236 A2 | 5/2012 |
| WO | 2013/004639 A2 | 1/2013 |

OTHER PUBLICATIONS

Churakova et al., Angew. Chem. Int. Ed., vol. 50, pp. 10716-10719 (2011).
Geigert et al., Biochemical and Biophysical Research Communications, vol. 136, No. 2, pp. 778-782 (1986).
Hu et al., Tetrahedron Letters, vol. 40, No. 9, pp. 1641-1644 (1999).
Kluge et al., Applied Microbiology and Biotechnology, vol. 75, pp. 1473-1478 (2007).
Kluge et al., Applied Microbiology and Biotechnology, vol. 81, No. 6, pp. 1071-1076 (2009).
Kluge et al., Green Chemistry, vol. 14, No. 2, pp. 440-446 (2012).
Peter et al., Enzyme and Microbial Technology, vol. 52, No. 6-7, pp. 370-376 (2013).
Piazza et al., Journal of Molecular Catalysis B Enzymatic, vol. 21, No. 3, pp. 143-151 (2003).
Ullrich et al., Applied and Environmental Microbiology, vol. 70, No. 8, pp. 4575-4581 (2004).
Ullrich et al., FEBS Letters, vol. 579, pp. 6247-6250 (2005).
Piontek et al., Acta. Cryst F66, 693-698 (2010).
Anonymous, DSM-22459 website (2017).

* cited by examiner

*Primary Examiner* — Suzanne M Noakes
(74) *Attorney, Agent, or Firm* — Eric J. Fechter

(57) ABSTRACT

The invention relates to enzymatic methods for epoxidation of a non-cyclic aliphatic alkene, or a terpene.

18 Claims, No Drawings

EPOXIDATION USING PEROXYGENASE

CROSS-REFERENCE TO RELATED APPLICATIONS

This application is a divisional of U.S. application Ser. No. 15/250,290 filed on Aug. 29, 2016, now U.S. Pat. No. 9,663,806, which is a divisional of U.S. application Ser. No. 14/382,957 filed on Sep. 4, 2014, now U.S. Pat. No. 9,458,478, which is a 35 U.S.C. 371 national application of international application no. PCT/EP2013/056326 filed on Mar. 25, 2013, which claims priority or the benefit under 35 U.S.C. 119 of European application nos. 12162791.3 and 12165214.3 filed on Mar. 31, 2012 and Apr. 23, 2012, respectively, and U.S. provisional application Nos. 61/622, 686 and 61/636,956 filed on Apr. 11, 2012 and Apr. 23, 2012, respectively. The content of these applications is fully incorporated herein by reference.

CROSS-REFERENCE TO A SEQUENCE LISTING

This application contains a Sequence Listing in computer readable form, which is incorporated herein by reference.

BACKGROUND OF THE INVENTION

Field of the Invention

The present invention relates to use of peroxygenases for epoxidation of non-cyclic aliphatic alkenes, or terpenes.

Background

A peroxygenase denoted AaP from the agaric basidiomycete strain *Agrocybe aegerita* (strain TM-A1) was found to oxidize aryl alcohols and aldehydes. The AaP peroxygenase was purified from *A. aegerita* TM A1 by several steps of ion chromatography, the molecular weight was determined by SDS-PAGE and the N-terminal 14 amino acid sequence was determined after 2-D electrophoresis but the encoding gene was not isolated (Ullrich et al., 2004, *Appl. Env. Microbiol.* 70(8): 4575-4581).

WO 2006/034702 discloses methods for the enzymatic hydroxylation of non-activated hydrocarbons, such as, naphtalene, toluol and cyclohexane, using the AaP peroxygenase enzyme of *Agrocybe aegerita* TM A1. This is also described in Ullrich and Hofrichter, 2005, *FEBS Letters* 579: 6247-6250.

WO 2008/119780 discloses eight different peroxygenases from *Agrocybe aegerita, Coprinopsis cinerea, Laccaria bicolor* and *Coprinus radians*.

DE 103 32 065 A1 discloses methods for the enzymatic preparation of acids from alcohols through the intermediary formation of aldehydes by using the AaP peroxygenase enzyme of *Agrocybe aegerita* TM A1.

A method was reported for the rapid and selective spectrophotometric direct detection of aromatic hydroxylation by the AaP peroxygenase (Kluge et al., 2007, *Appl. Microbiol. Biotechnol.* 75: 1473-1478).

It is well-known that a direct regioselective introduction of oxygen functions (oxygenation) into organic molecules constitutes a problem in chemical synthesis. The products may be used as important intermediates in a wide variety of different syntheses.

It is known that an intracellular enzyme, methane monooxygenase (MMO, EC 14.13.25), oxygenates/hydroxylates the terminal carbon of some hydrocarbons. The MMO enzyme consists of several protein components and is solely formed by methylotrophic bacteria (e.g. *Methylococcus capsulatus*); it requires complex electron donors such as NADH or NADPH, auxiliary proteins (flavin reductases, regulator protein) and molecular oxygen ($O_2$). The natural substrate of MMO is methane, which is oxidized to methanol. As a particularly unspecific biocatalyst, MMO oxygenates/hydroxylates, as well as methane, a series of further substrates such as n-alkanes and their derivatives, cycloalkanes, aromatics, carbon monoxide and heterocycles. Utilization of the enzyme in biotechnology is currently not possible, since it is difficult to isolate, like most intracellular enzymes, it is of low stability, and the cosubstrates required are relatively expensive.

SUMMARY OF THE INVENTION

In a first aspect, the inventors of the present invention have provided an enzymatic method for producing an epoxide, comprising contacting a non-cyclic aliphatic alkene, or a terpene, with hydrogen peroxide and a peroxygenase; wherein the peroxygenase comprises an amino acid sequence which has at least 60% identity to SEQ ID NO: 1, 2, 3, 4, 5, 6, 7, 8, 9, 10, 11, 12, 13, 14, 15, 16, 17, 18, 19, or 20. In an embodiment, the amino acid sequence comprises the motif: E-H-D-[G,A]-S-[L,I]-S-R (SEQ ID NO: 21).

Definitions

Peroxygenase activity: The term "peroxygenase activity" means an "unspecific peroxygenase" activity according to EC 1.11.2.1, that catalyzes insertion of an oxygen atom from $H_2O_2$ into a variety of substrates, such as nitrobenzodioxole. For purposes of the present invention, peroxygenase activity is determined according to the procedure described in Poraj-Kobielska et al., 2012, "A spectrophotometric assay for the detection of fungal peroxygenases", *Analytical Biochemistry* 421(1): 327-329.

The peroxygenase of the present invention has at least 20%, preferably at least 40%, more preferably at least 50%, more preferably at least 60%, more preferably at least 70%, more preferably at least 80%, even more preferably at least 90%, most preferably at least 95%, and even most preferably at least 100% of the peroxygenase activity of the mature polypeptide of SEQ ID NO: 1, 2, 3, 4, 5, 6, 7, 8, 9, 10, 11, 12, 13, 14, 15, 16, 17, 18, 19, or 20.

Mature polypeptide: The term "mature polypeptide" is defined herein as a polypeptide having peroxygenase activity that is in its final form following translation and any post-translational modifications, such as N-terminal processing, C-terminal truncation, glycosylation, phosphorylation, etc. In a preferred aspect, the mature polypeptide has the amino acid sequence shown in positions 1 to 328 of SEQ ID NO:1 based on the N-terminal peptide sequencing data (Ullrich et al., 2004, *Appl. Env. Microbiol.* 70(8): 4575-4581), elucidating the start of the mature protein of AaP peroxygenase enzyme.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; emboss.org), preferably version 3.0.0 or later. The optional parameters used are gap open penalty of 10, gap extension penalty of 0.5, and the EDNA-FULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

Modification: The term "modification" means herein any chemical modification of the polypeptide consisting of the mature polypeptide of SEQ ID NO: 1, 2, 3, 4, 5, 6, 7, 8, 9, 10, 11, 12, 13, 14, 15, 16, 17, 18, 19, or 20; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

DETAILED DESCRIPTION OF THE INVENTION

Peroxygenase

The present invention relates to methods for epoxidation using a polypeptide, which is preferably recombinantly produced, having peroxygenase activity (referenced as "peroxygenase"), which comprises or consists of an amino acid sequence having at least 60% identity, preferably at least 65%, 70%, 75%, 80%, 85%, 90%, 95%, 97%, 98%, or 99% identity to the polypeptide of SEQ ID NO: 1, 2, 3, 4, 5, 6, 7, 8, 9, 10, 11, 12, 13, 14, 15, 16, 17, 18, 19, or 20; preferably SEQ ID NO: 1.

In a preferred embodiment, the peroxygenase comprises an amino acid sequence represented by the motif: E-H-D-[G,A]-S-[L,I]-S-R (SEQ ID NO: 21).

In yet another embodiment, the polypeptide of the first aspect comprises or consists of the amino acid sequence of SEQ ID NO: 1, 2, 3, 4, 5, 6, 7, 8, 9, 10, 11, 12, 13, 14, 15, 16, 17, 18, 19, or 20; preferably SEQ ID NO: 1; or a fragment thereof having peroxygenase activity; preferably the polypeptide comprises or consists of the mature polypeptide of SEQ ID NO: 1, 2, 3, 4, 5, 6, 7, 8, 9, 10, 11, 12, 13, 14, 15, 16, 17, 18, 19, or 20; preferably SEQ ID NO: 1.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., peroxygenase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and regiondirected mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 1, 2, 3, 4, 5, 6, 7, 8, 9, 10, 11, 12, 13, 14, 15, 16, 17, 18, 19, or 20; preferably SEQ ID NO: 1; is 10, preferably 9, more preferably 8, more preferably 7, more preferably at most 6, more preferably 5, more preferably 4, even more preferably 3, most preferably 2, and even most preferably 1.

Hydrogen Peroxide

The hydrogen peroxide required by the peroxygenase may be provided as an aqueous solution of hydrogen peroxide or a hydrogen peroxide precursor for in situ production of hydrogen peroxide. Any solid entity which liberates upon dissolution a peroxide, which is useable by peroxygenase, can serve as a source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3._, EC 1.2.3._, EC 1.4.3._, and EC 1.5.3._ or similar classes (under the International Union of Biochemistry), other examples of such combinations of oxidases and substrates are easily recognized by one skilled in the art.

Alternative oxidants which may be applied for peroxygenases may be oxygen combined with a suitable hydrogen donor like ascorbic acid, dehydroascorbic acid, dihydroxyfumaric acid or cysteine. An example of such oxygen hydrogen donor system is described by Pasta et al., 1999, *Biotechnology & Bioengineering* 62(4): 489-493.

Hydrogen peroxide or a source of hydrogen peroxide may be added at the beginning of or during the method of the invention, e.g. as one or more separate additions of hydrogen peroxide; or continously as fed-batch addition. Typical amounts of hydrogen peroxide correspond to levels of from 0.001 mM to 25 mM, preferably to levels of from 0.005 mM to 5 mM, and particularly to levels of from 0.01 to 1 mM or 0.02 to 2 mM hydrogen peroxide. Hydrogen peroxide may also be used in an amount corresponding to levels of from 0.1 mM to 25 mM, preferably to levels of from 0.5 mM to 15 mM, more preferably to levels of from 1 mM to 10 mM, and most preferably to levels of from 2 mM to 8 mM hydrogen peroxide.

Surfactants

The method of the invention may include application of a surfactant (for example, as part of a detergent formulation or as a wetting agent). Surfactants suitable for being applied may be non-ionic (including semi-polar), anionic, cationic and/or zwitterionic; preferably the surfactant is anionic (such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap) or non-ionic (such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides")), or a mixture thereof.

When included in the method of the invention, the concentration of the surfactant will usually be from about 0.01% to about 10%, preferably about 0.05% to about 5%, and more preferably about 0.1% to about 1% by weight.

Aliphatic Alkene

The aliphatic alkene (unsaturated aliphatic hydrocarbon), which is epoxidized in the method of the invention, is a non-cyclic aliphatic alkene, which is linear or branched; and substituted or unsubstituted. Preferably, the aliphatic alkene is unsubstituted. Branched alkenes correspond to isomers of linear alkenes.

In an embodiment, the non-cyclic aliphatic alkene has at least three carbons. In another embodiment, the aliphatic alkene has a carbon-carbon double bond (an unsaturated carbon) at one end.

Preferably, the aliphatic alkene is propene, butene, pentene, hexene, heptene, octene, nonene, decene, undecene, dodecene, tridecene, tetradecene, pentadecene or hexadecene, or isomers thereof. More preferably, the aliphatic akene is propene, 1-butene, 1-pentene, 1-hexene, 2-hexene, 3-hexene, 1-heptene, 1-octene, 2-methyl-2-butene, 2,3-dimethyl-2-butene, cis/trans-2-butene, isobutene, 1,3-butadiene, and isoprene; or isomers thereof.

When the aliphatic alkenes are substituted (functional groups attached), the preferred substituents are halogen, hydroxyl, carboxyl, amino, nitro, cyano, thiol, sulphonyl, formyl, acetyl, methoxy, ethoxy, carbamoyl and sulfamoyl; more preferred substituents are chloro, hydroxyl, carboxyl and sulphonyl; and most preferred substituents are chloro and carboxyl.

The aliphatic alkenes may be substituted by up to 10 substituents, up to 8 substituents, up to 6 substituents, up to 4 substituents, up to 2 substituents, or by up to one substituent.

Terpene

The terpenes, which are epoxidized according to the invention, include isoprene, and compounds having multiples of the isoprene structure. The terpenes of the invention also include terpenoids.

Terpenes can be subdivided in monoterpenes (two isoprene units), sesquiterpenes (three isoprene units), diterpenes (four isoprene units), triterpenes (six isoprene units), tetraterpenes (eight isoprene units) etc. Terpenes can be monocyclic, bicyclic, tricyclic, etc. Examples of monoterpenes include geraniol (rose oil) and monocyclic monoterpenes, such as (−)-menthol (peppermint oil), R-(+)-carvone (caroway oil), S-(−)-carvone (spearmint oil), R-(+)-limonene (orange oil), and S-(−)-limonene (pine oil smell).

Preferably the terpene of the invention is isoprene or a monoterpene; more preferably the terpene is a cyclic terpene, such as a monocyclic monoterpene, such as limonene.

Terpenes and cyclic terpenes like limonene are found broadly in nature. Limonene is the most abundant common naturally occurring terpene—produced by more than 300 plants and is a major component in citrus peel oil. Epoxidation of limonene is of particular relevance since it forms the basis for the synthesis of fragrances and drugs. Peroxygenases epoxidize limonene both in the ring position and in the side chain—with dominating preference for the ring position (see Example 1).

Methods and Uses

The present invention provides a method for producing an epoxide from a non-cyclic aliphatic alkene, or a terpene (a method for epoxidation of a non-cyclic aliphatic alkene or a terpene), comprising contacting the aliphatic alkene, or terpene, with a peroxygenase and hydrogen peroxide. Thus, the invention provides a method for converting a non-cyclic aliphatic alkene, or terpene, to an epoxide, by oxidation of the aliphatic alkene or terpene at a carbon-carbon double bond.

The aliphatic alkene includes at least three carbons. Preferably, the aliphatic alkene has a carbon-carbon double bond (an unsaturated carbon) at one end.

Accordingly, in a first aspect, the present invention provides a method for producing an epoxide, comprising contacting a non-cyclic aliphatic alkene, or terpene, with hydrogen peroxide and a peroxygenase; wherein the peroxygenase comprises an amino acid sequence which has at least 60% identity to SEQ ID NO: 1, 2, 3, 4, 5, 6, 7, 8, 9, 10, 11, 12, 13, 14, 15, 16, 17, 18, 19, or 20. The aliphatic alkene may be substituted or unsubstituted, linear or branched.

In an embodiment, the amino acid sequence comprises the motif: E-H-D-[G,A]-S-[L,I]-S-R (SEQ ID NO: 21).

In an embodiment, the peroxygenase comprises or consists of an amino acid sequence having at least 65% identity, preferably at least 70% identity, more preferably at least 75% identity, more preferably at least 80% identity, more preferably at least 85% identity, most preferably at least 90% identity, and in particular at least 95% identity to the amino acid sequence of SEQ ID NO: 1, 2, 3, 4, 5, 6, 7, 8, 9, 10, 11, 12, 13, 14, 15, 16, 17, 18, 19, or 20; preferably SEQ ID NO: 1. In a preferred embodiment, the peroxygenase comprises or consists of the amino acid sequence of SEQ ID NO: 1, 2, 3, 4, 5, 6, 7, 8, 9, 10, 11, 12, 13, 14, 15, 16, 17, 18, 19, or 20; preferably SEQ ID NO: 1; or a fragment thereof having peroxygenase activity.

In an embodiment, the terpene is isoprene or a monoterpene; preferably the terpene is a cyclic terpene, such as a monocyclic monoterpene, such as limonene.

In another embodiment, the aliphatic alkene has one or more substituents selected from the group consisting of halogen, hydroxyl, carboxyl, amino, nitro, cyano, thiol, sulphonyl, formyl, acetyl, methoxy, ethoxy, carbamoyl and sulfamoyl. Preferably, the substituent(s) are selected from the group consisting of chloro, hydroxyl, carboxyl and sulphonyl; in particular, chloro and carboxyl.

In another embodiment, the aliphatic alkene consists of at least three carbons, and has a carbon-carbon double bond at one end.

In another embodiment, the aliphatic alkene is propene, butene, pentene, hexene, heptene, octene, nonene, decene, undecene, dodecene, tridecene, tetradecene, pentadecene or hexadecene, or isomers thereof. In a more preferred embodiment, the aliphatic alkene is propene, 1-butene, 1-pentene, 1-hexene, 2-hexene, 3-hexene, 1-heptene, 1-octene, 2-methyl-2-butene, 2,3-dimethyl-2-butene, cis/trans-2-butene, isobutene, 1,3-butadiene, and isoprene; or isomers thereof.

In another embodiment, the aliphatic alkene is unsubstituted.

In another embodiment, the aliphatic alkene is linear.

Preferred epoxides, which can be produced by the method of the invention include, but are not limited to, propylene oxide (1,2-epoxypropane) and epoxy terpenes (including epoxy terpenoids), such as limonene oxide; and 2-methyloxirane, 2-ethyloxirane, 2-propyloxirane, 2-butyloxirane, 2-pentyloxirane, 2-hexyloxirane, 2,2,3-trimethyloxirane, 2,2,3,3-tetramethyloxirane, (2S,3S)-2,3-dimethyloxirane, (2R,3S)-2,3-Dimethyloxirane, 2,2-dimethyloxirane, 2-methyl-2-(4-methylcyclohex-3-en-1-yl)oxirane, 2-methyl-2-(4-methylcyclohex-3-en-1-yl)oxirane, 2-ethenyloxirane, 2-ethenyl-2-methyloxirane, 2-methyl-3-propyloxirane, and 2,3-diethyloxirane.

The method of the invention may be used for a variety of purposes, like bulk chemical synthesis (biocatalysis). Alkenes are efficiently epoxidized by peroxygenases. Propylene oxide is a highly reactive substance and one of the most important chemical intermediates. It is the starting material for a broad spectrum of products, including polymers (polyurethanes, polyesters), oxygenated solvents (propylene glycol ethers) and industrial fluids (monopropylene glycol and polyglycols). Annually 6,500,000 MT are produced. Other longer chain alkenes including branched alkenes are epoxidized in a similar manner—including butene and isobutene.

Polymerization of an epoxide gives a polyether, for example ethylene oxide polymerizes to give polyethylene glycol, also known as polyethylene oxide.

The methods of the invention may be carried out with an immobilized peroxygenase.

The methods of the invention may be carried out in an aqueous solvent (reaction medium), various alcohols, ethers, other polar or non-polar solvents, or mixtures thereof. By studying the characteristics of the aliphatic hydrocarbon used in the methods of the invention, suitable examples of solvents are easily recognized by one skilled in the art. By raising or lowering the pressure at which the oxidation is carried out, the solvent (reaction medium) and the aliphatic hydrocarbon can be maintained in a liquid phase at the reaction temperature.

The methods according to the invention may be carried out at a temperature between 0 and 90° C., preferably between 5 and 80° C., more preferably between 10 and 70° C., even more preferably between 15 and 60° C., most preferably between 20 and 50° C., and in particular between 20 and 40° C.

The methods of the invention may employ a treatment time of from 10 seconds to (at least) 24 hours, preferably from 1 minute to (at least) 12 hours, more preferably from 5 minutes to (at least) 6 hours, most preferably from 5 minutes to (at least) 3 hours, and in particular, from 5 minutes to (at least) 1 hour.

The present invention is further described by the following examples that should not be construed as limiting the scope of the invention.

EXAMPLES

The amino acid sequence of the peroxygenase from *Agrocybe aegerita* is shown as SEQ ID NO: 1.

Example 1

Alkene Epoxidation Catalyzed by a Fungal Peroxygenase

Reagents

Commercially available chemicals were purchased from Sigma-Aldrich, TCI Europe and Chemos GmbH, except for 2,3-epoxy-2-methylbutane which was purchased from Acros Organics. The extracellular peroxygenase of *Agrocybe aegerita* (wild type, isoform II, 44 kDa) was produced and purified as described previously. The enzyme preparation was homogeneous by SDS polyacrylamide gel electrophoresis and exhibited an $A_{418}/A_{280}$ ratio of 1.86. The specific activity of the peroxygenase was 63 U mg$^{-1}$, where 1 U represents the oxidation of 1 μmol of 3,4-dimethoxybenzyl alcohol to 3,4-dimethoxybenzaldehyde in 1 min at 23° C.

Reaction Conditions

Typical reaction mixtures (total volume: 0.2 ml; 1.2 ml for gaseous alkenes) contained purified peroxygenase (1-2 U ml$^{-1}$, 0.38-0.76 μM) dissolved in potassium phosphate buffer (10 mM, pH 7.0), acetone (60%, pH 5.3), and the alkene substrate (5% vol/vol; except for +/− limonene 5 mM of the substrate was used). The reactions were started by the addition of H$_2$O$_2$ via a syringe pump (4 mM h$^{-1}$, except for 2-methyl-2-butene and 2,3-dimethyl-2-butene 2 mM h$^{-1}$ was used), stirred at room temperature for 30 min, and stopped at which time chromatographic analyses showed that product formation was complete. Gaseous propene and n-butene were treated under the same conditions but by continuously bubbling the pure gas through the reaction vial (approx. 1 l h$^{-1}$). The reaction mixtures were extracted with hexane (0.1 ml) by vigorous shaking.

Product Identification

The reaction products were analyzed by GC using a Hewlett Packard 6890 chromatograph equipped with a Hewlett Packard 5973 mass spectrometer and a ZB-Wax plus capillary column (250 μm diameter by 30 m length, 0.25 μm film thickness, Phenomenex, Torrance, Calif., USA). For analysis, 1 μl of the hexane extract was injected into the GC-system. GC was performed using various temperature profiles in dependence of the analyte. Propene: 30° C. hold 2 min; 1-butene: 35° C. hold 3.5 min, 30° C. min$^{-1}$ to 100° C.; 1-pentene: 50° C. hold 3.5 min, 40° C. min$^{-1}$ to 115° C.; 1-hexene, 2-hexene and 3-hexene: 70° C. hold 3.5 min, 40° C. min$^{-1}$ to 135° C.; 1-heptene: 90° C. hold 3.5 min, 40° C. min$^{-1}$ 145° C.; 1-octene: 110° C. hold 3.5 min, 20° C. min$^{-1}$ to 120° C.; +/−limonene: 70° C., 5° C. min$^{-1}$ to 125° C., 30° C. min$^{-1}$ to 230° C.; cis/trans-2-butene, isobutene and 1,3-butadiene: 35° C. hold 10 min; cyclopentene and cycloheptene: 45° C. hold 3 min, 20° C. min$^{-1}$ to 250° C.; isoprene: 45° C. hold 5 min, 10° C. min$^{-1}$ to 100° C. Helium was the carrier gas, in all cases, at a column flow rate of 1.5 ml min$^{-1}$. The products were identified relative to authentic standards by their retention times and/or by electron impact MS at 70 eV.

Chiral Separation

The chiral separation of epoxides was performed by GC/MS using the above apparatus but fitted with a Beta DEX™ 120 capillary column (250 μm in diameter by 30 m length, 0.25 μm film thickness, Supelco, Bellefonte, Pa., USA). GC was performed using various temperature profiles. 1-hexene: 45° C. hold 20 min; 1-heptene: 45° C. hold 37 min; 1-octene: 55° C. hold 46 min; 1-octyne: 45° C. hold 2 min, 10° C./min to 155° C. The products were identified relative to authentic standards by their retention time and by electron impact MS at 70 eV.

Product Quantification

Quantitative analyses of the reaction products were performed by GC/MS as described above, using external standard curves of the respective authentic standards. All standard curves had linear regression values of $R^2 > 0.98$.

Results

TABLE 1 A

| No. | Substrate | Alcohol Product | Amount (μM) | Epoxide Product | Amount (μM) | Total Product (μM) | Epoxide (%) |
|---|---|---|---|---|---|---|---|
| 1 | (propene) | — | — | (epoxide) | 117 | 117 | 100 |
| 2 | (1-butene) | OH | 20 | (epoxide) | 60 | 80 | 75 |
| 3 | (1-pentene) | OH | 28 | (epoxide) | 12 | 40 | 31 |
| 4 | (1-hexene) | OH | 6 | (epoxide) | 6 | 12 | 50 |
| 5 | (1-heptene) | OH | 1 | (epoxide) | 9 | 10 | 88 |
| 6 | (1-octene) | OH | 88 | (epoxide) | 106 | 194 | 55 |
| 7 | (2-methyl-2-butene) | — | — | (epoxide) | 989 | 989 | 100 |
| 8 | (2,3-dimethyl-2-butene) | — | — | (epoxide) | 496 | 496 | 100 |

TABLE 1A-continued

| No. | Substrate | Alcohol Product | Amount (μM) | Epoxide Product | Amount (μM) | Total Product (μM) | Epoxide (%) |
|---|---|---|---|---|---|---|---|
| 9 | (propene) | — | — | (methyloxirane) | 900 | 900 | 100 |
| 10 | (cis-2-butene) | — | — | (2,3-dimethyloxirane) | 1910 | 1910 | 100 |
| 11 | (isobutene) | — | — | (2,2-dimethyloxirane) | 912 | 912 | 100 |
| 12 | (limonene) | (carveol) | 247 | (limonene oxides) | 460/309 | 1020 | 76 (46/30) |
| 13 | (limonene isomer) | (carveol) | 163 | (limonene oxides) | 561/360 | 1084 | 85 (52/33) |
| 14 | (1,3-butadiene) | — | — | (vinyloxirane) | nd | nd | nd |
| 15 | (isoprene) | — | — | (isoprene epoxides) | nd | nd | nd |
| 16 | (1-pentene chain) | nd | nd | (epoxide) | nd | nd | nd |
| 17 | (2-pentene) | nd | nd | (epoxide) | nd | nd | nd |
| 18 | (cyclopentene) | nd | nd | (cyclopentene oxide) | nd | nd | nd |
| 19 | (cycloheptene) | nd | nd | (cycloheptene oxide) | nd | nd | nd |

"nd" means that the reaction was carried out and the product was identified, but the product yield was not determined.

TABLE 1B

| Substrate No. | IUPAC name of the respective epoxide products (the formulae are given in column 5 of table 1A) |
|---|---|
| 1 | 2-methyloxirane |
| 2 | 2-ethyloxirane |
| 3 | 2-propyloxirane |
| 4 | 2-butyloxirane |
| 5 | 2-pentyloxirane |
| 6 | 2-hexyloxirane |
| 7 | 2,2,3-trimethyloxirane |
| 8 | 2,2,3,3-tetramethyloxirane |
| 9 | (2S,3S)-2,3-dimethyloxirane |
| 10 | (2R,3S)-2,3-Dimethyloxirane |
| 11 | 2,2-dimethyloxirane |
| 12 | (4R,6R)-1-methyl-4-(prop-1-en-2-yl)-7-oxabicyclo[4.1.0]heptane/2-methyl-2-(4-methylcyclohex-3-en-1-yl)oxirane |
| 13 | (4S,6R)-1-methyl-4-(prop-1-en-2-yl)-7-oxabicyclo[4.1.0]heptane/2-methyl-2-(4-methylcyclohex-3-en-1-yl)oxirane |
| 14 | 2-ethenyloxirane |
| 15 | 2-ethenyl-2-methyloxirane/2-(prop-1-en-2-yl)oxirane |
| 16 | 2-methyl-3-propyloxirane |
| 17 | 2,3-diethyloxirane |
| 18 | 6-oxabicyclo[3.1.0]hexane |
| 19 | 8-oxabicyclo[5.1.0]octane |

Example 2

Epoxidation of 1-Octene Using Different Fungal Peroxygenases

The peroxygenases shown in Table 2 were used in Example 2.

TABLE 2

| Name | Source organism | Amino acid sequence |
|---|---|---|
| Peroxygenase 1 | Coprinopsis cinerea | SEQ ID NO: 2 |
| Peroxygenase 2 | Chaetomium virescens | SEQ ID NO: 7 |
| Peroxygenase 3 | Humicola insolens | SEQ ID NO: 8 |
| Peroxygenase 4 | Chaetomium globosum | SEQ ID NO: 9 |
| Peroxygenase 5 | Daldinia caldariorum | SEQ ID NO: 14 |
| Peroxygenase 6 | Myceliophthora fergusii | SEQ ID NO: 15 |
| Peroxygenase 7 | Myceliophthora hinnulea | SEQ ID NO: 16 |
| Peroxygenase 8 | Thielavia hyrcaniae | SEQ ID NO: 18 |
| Peroxygenase 9 | Pestalotiopsis virgatula | SEQ ID NO: 19 |

Reactions were carried out in capped 2 mL HPLC glass vials at the following conditions: 10 mM phosphate buffer pH 6.5, 20% v/v acetonitrile, 1 mM 1-octene, 0.01 mg/mL peroxygenase (see Table 3), 1 mM hydrogen peroxide, in a total reaction volume of 800 µL. Reaction mixtures were stirred by magnet at room temperature (~25° C.) for 30 minutes, and the reaction was stopped by adding 5 µL catalase (Terminox Ultra 50L, Novozymes).

Samples were extracted by mixing with 760 µL ethyl acetate containing 0.01% w/v BHT (2,6-di-tert-butyl-4-methylphenol). The ethyl acetate extracts were analyzed by GC-MS on a gas chromatograph (model 7890A) equipped with an autosampler (model 7693A) and a mass selective detector (model 5975C) from Agilent (Santa Clara Calif., USA) as follows: samples were injected in split mode (10:1) on a Zebron DB-5HT Inferno column (15 m, 250 µm, 0.25 µm) from Phenomenex (Torrance Calif., USA) and eluted with 1.1 mL/min Helium using the following temperature program: 45° C. (for 1 min), 45-75° C. at 10° C./min, 75-275° C. at 40° C./min and 275° C. (1 minute). The mass detector was operated in scan mode and the Total Ion Count (TIC) chromatogram was used to determine the areas of the substrate and product peaks. Peaks were identified by comparing the mass spectra with spectra from the mass spectral library available in the GC software (NIST MS search version 2.0). Substrate and product concentrations were determined by external calibration with authentic compounds using BHT (2,6-di-tert-butyl-4-methylphenol) as internal standard.

The enzymatic conversion of 1-octene (substrate) to 1,2-epoxyoctane (product) is shown in Table 3. Due to the volatility of 1-octene, a large part of the substrate was lost by evaporation during the reaction.

TABLE 3

Concentration of remaining substrate and reaction product when reaction was stopped.

| Enzyme | Concentration of 1-octene (mM) | Concentration of 1,2-epoxyoctane (mM) |
|---|---|---|
| Peroxygenase 1 | 0.07 | 0.02 |
| Peroxygenase 2 | 0.09 | 0.02 |
| Peroxygenase 3 | 0.07 | 0.19 |
| Peroxygenase 4 | 0.10 | 0.01 |
| Peroxygenase 5 | 0.10 | 0.01 |
| Peroxygenase 6 | 0.07 | 0.02 |
| Peroxygenase 7 | 0.12 | 0.02 |
| Peroxygenase 8 | 0.09 | 0.04 |
| Peroxygenase 9 | 0.12 | 0.01 |

Example 3

Epoxidation of Different Alkenes Using a *Humicola* Peroxygenase

Reactions were carried out in capped 2 mL HPLC glass vials at the following conditions: 10 mM phosphate buffer pH 6.5, 20% v/v acetonitrile, 1 mM substrate (see Table 4), 0.01 mg/mL of peroxygenase 3 (see Example 2), 1 mM hydrogen peroxide, in a total reaction volume of 800 µL. Reaction mixtures were stirred by magnet at room temperature (~25° C.) for 30 minutes, and the reaction was stopped by adding 5 µL catalase (Terminox Ultra 50L, Novozymes).

Samples were extracted by mixing with 760 µL ethyl acetate containing 0.01% w/v BHT (2,6-di-tert-butyl-4-methylphenol) as internal standard. The ethyl acetate extracts were analyzed by GC-MS as described in Example 2. Due to lack of authentic standards and high volatility of some substrates, product yields were calculated as the Area/Aistd of product in the sample compared to the Area/Aistd of a standard sample with 1 mM substrate dissolved in ethyl acetate containing 0.01% w/v BHT, assuming the same response factor for substrate and products. Results are shown in Table 4.

TABLE 4

Results for epoxidation of different alkenes using Peroxygenase 3.

| Substrate | Main product | Product yield |
|---|---|---|
| 1-Octene | 1,2-epoxyoctane | 15% |
| trans-2-Octene | 2,3-epoxyoctane | 63% |
| trans-3-Octene | 3,4-epoxyoctane | 69% |
| trans-4-Octene | 4,5-epoxyoctane | 76% |
| 1,9-Decadiene | 1,2-epoxy-9-decene | 13% |

Example 4

Epoxidation of Trans-2-Octene Using a *Humicola* Peroxygenase

Reactions were carried out in capped 2 mL HPLC glass vials under the following conditions: 10 mM phosphate buffer pH 6.5, 20% v/v acetonitrile, 20 g/L trans-2-octene, 0.1 or 0.5 mg/mL of peroxygenase 3 (see Example 2), 160 µL of 1 M hydrogen peroxide dosed during the reaction (2 hours) with a multi-channel syringe pump (model 220-CE, World precision instruments, Aston, Stevenage, UK) using 1 mL gas tight glass syringes (SGE Analytical Science, Ringwood, Australia); in a final reaction volume of 800 µL. Reaction mixtures were stirred by magnet at room temperature (~25° C.) for 2 hours, and the reaction was stopped by adding 5 µL catalase (Terminox Ultra 50L, Novozymes).

Samples were extracted by mixing with 780 µL ethyl acetate containing 0.1% w/v BHT (2,6-di-tert-butyl-4-methylphenol) as internal standard. The ethyl acetate extracts were diluted 100 times with ethyl acetate without internal standard and analyzed by GC-MS as reported in Example 2.

Formation of epoxide was measured as the area percentage of epoxide compared to the area sum of substrate and products, assuming the same response factor for substrate and product.

TABLE 5

Results from epoxidation of trans-3-octene using Peroxygenase 3.

| Peroxygenase concentration | Yield of 2,3-epoxyoctane |
|---|---|
| 0 mg/mL | 0% |
| 0.1 mg/mL | 3% |
| 0.5 mg/mL | 40% |

The invention claimed is:

1. A method for producing an epoxide, comprising contacting a non-cyclic aliphatic alkene or a terpene with hydrogen peroxide and a peroxygenase (EC 1.11.2.1), wherein the peroxygenase comprises an amino acid sequence having at least 90% sequence identity to SEQ ID NO: 1.

2. The method of claim 1, wherein the peroxygenase comprises an amino acid sequence having at least 95% sequence identity to SEQ ID NO: 1.

3. The method of claim 1, wherein the peroxygenase comprises an amino acid sequence having at least 97% sequence identity to SEQ ID NO: 1.

4. The method of claim 1, wherein the peroxygenase comprises an amino acid sequence having at least 98% sequence identity to SEQ ID NO: 1.

5. The method of claim 1, wherein the peroxygenase comprises an amino acid sequence having at least 99% sequence identity to SEQ ID NO: 1.

6. The method of claim 1, wherein the peroxygenase comprises the amino acid sequence of SEQ ID NO: 1.

7. The method of claim 1, wherein the amino acid sequence comprises the motif E-H-D-[G,A]-S-[L,I]-S-R (SEQ ID NO: 21).

8. The method of claim 1, wherein the aliphatic alkene has one or more substituents selected from the group consisting of halogen, hydroxyl, carboxyl, amino, nitro, cyano, thiol, sulphonyl, formyl, acetyl, methoxy, ethoxy, carbamoyl and sulfamoyl.

9. The method of claim 8, wherein the substituent(s) are selected from the group consisting of chloro, hydroxyl, carboxyl and sulphonyl.

10. The method of claim 1, wherein the aliphatic alkene consists of at least three carbons, and has a carbon-carbon double bond at one end.

11. The method of claim 1, wherein the aliphatic alkene is propene, butene, pentene, hexene, heptene, octene, nonene, decene, undecene, dodecene, tridecene, tetradecene, pentadecene, or hexadecene, or an isomer thereof.

12. The method of claim 1, wherein the aliphatic alkene is propene, 1-butene, 1-pentene, 1-hexene, 2-hexene, 3-hexene, 1-heptene, 1-octene, 2-methyl-2-butene, 2,3-dimethyl-2-butene, cis/trans-2-butene, isobutene, 1,3-butadiene, and isoprene; or an isomer thereof.

13. The method of claim 1, wherein the aliphatic alkene is unsubstituted.

14. The method of claim 1, wherein the aliphatic alkene is linear.

15. The method of claim 1, wherein the terpene is isoprene or a monoterpene.

16. The method of claim 1, wherein the terpene is a cyclic terpene.

17. The method of claim 16, wherein the cyclic terpene is a monocyclic monoterpene.

18. The method of claim 17, wherein the monocyclic monoterpene is limonene.

* * * * *

SEQUENCE LISTING

```
<160> NUMBER OF SEQ ID NOS: 21

<210> SEQ ID NO 1
<211> LENGTH: 328
<212> TYPE: PRT
<213> ORGANISM: Agrocybe aegerita
<220> FEATURE:
<221> NAME/KEY: mat_peptide
<222> LOCATION: (1)..(328)

<400> SEQUENCE: 1

Glu Pro Gly Leu Pro Pro Gly Pro Leu Glu Asn Ser Ser Ala Lys Leu
1               5                   10                  15

Val Asn Asp Glu Ala His Pro Trp Lys Pro Leu Arg Pro Gly Asp Ile
            20                  25                  30

Arg Gly Pro Cys Pro Gly Leu Asn Thr Leu Ala Ser His Gly Tyr Leu
        35                  40                  45

Pro Arg Asn Gly Val Ala Thr Pro Val Gln Ile Ile Asn Ala Val Gln
    50                  55                  60

Glu Gly Leu Asn Phe Asp Asn Gln Ala Ala Val Phe Ala Thr Tyr Ala
65                  70                  75                  80

Ala His Leu Val Asp Gly Asn Leu Ile Thr Asp Leu Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
        115                 120                 125

Arg Gly Asp Ala Phe Phe Gly Asn Asn His Asp Phe Asn Glu Thr Leu
    130                 135                 140

Phe Glu Gln Leu Val Asp Tyr Ser Asn Arg Phe Gly Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Thr
            180                 185                 190

Ala Tyr Gly Glu Thr Thr Phe Pro Ala Asn Leu Phe Val Asp Gly Arg
        195                 200                 205

Arg Asp Asp Gly Gln Leu Asp Met Asp Ala Ala Arg Ser Phe Gln
    210                 215                 220

Phe Ser Arg Met Pro Asp Asp Phe Phe Arg Ala Pro Ser Pro Arg Ser
225                 230                 235                 240

Gly Thr Gly Val Glu Val Val Ile Gln Ala His Pro Met Gln Pro Gly
                245                 250                 255
```

```
Arg Asn Val Gly Lys Ile Asn Ser Tyr Thr Val Asp Pro Thr Ser Ser
            260                 265                 270

Asp Phe Ser Thr Pro Cys Leu Met Tyr Glu Lys Phe Val Asn Ile Thr
        275                 280                 285

Val Lys Ser Leu Tyr Pro Asn Pro Thr Val His Val Arg Lys Ala Leu
    290                 295                 300

Asn Thr Asn Leu Asp Phe Phe Phe Gln Gly Val Ala Ala Gly Cys Thr
305                 310                 315                 320

Gln Val Phe Pro Tyr Gly Arg Asp
                325

<210> SEQ ID NO 2
<211> LENGTH: 344
<212> TYPE: PRT
<213> ORGANISM: Coprinopsis cinerea
<220> FEATURE:
<221> NAME/KEY: mat_peptide
<222> LOCATION: (1)..(344)

<400> SEQUENCE: 2

Thr Ser Lys Leu Pro Ile Val Phe Pro Pro Pro Glu Pro Ile
1               5                   10                  15

Lys Asp Pro Trp Leu Lys Leu Val Asn Asp Arg Ala His Pro Trp Arg
                20                  25                  30

Pro Leu Arg Arg Gly Asp Val Arg Gly Pro Cys Pro Gly Leu Asn Thr
            35                  40                  45

Leu Ala Ser His Gly Tyr Leu Pro Arg Asp Gly Val Ala Thr Pro Ala
        50                  55                  60

Gln Ile Ile Thr Ala Val Gln Glu Gly Phe Asn Met Glu Tyr Gly Ile
65                  70                  75                  80

Ala Thr Phe Val Thr Tyr Ala Ala His Leu Val Asp Gly Asn Pro Leu
                85                  90                  95

Thr Asn Leu Ile Ser Ile Gly Gly Lys Thr Arg Lys Thr Gly Pro Asp
            100                 105                 110

Pro Pro Pro Pro Ala Ile Val Gly Gly Leu Asn Thr His Ala Val Phe
        115                 120                 125

Glu Gly Asp Ala Ser Met Thr Arg Gly Asp Phe His Leu Gly Asp Asn
130                 135                 140

Phe Asn Phe Asn Gln Thr Leu Trp Glu Gln Phe Lys Asp Tyr Ser Asn
145                 150                 155                 160

Arg Tyr Gly Gly Gly Arg Tyr Asn Leu Thr Ala Ala Ala Glu Leu Arg
                165                 170                 175

Trp Ala Arg Ile Gln Gln Ser Met Ala Thr Asn Gly Gln Phe Asp Phe
            180                 185                 190

Thr Ser Pro Arg Tyr Phe Thr Ala Tyr Ala Glu Ser Val Phe Pro Ile
        195                 200                 205

Asn Phe Phe Thr Asp Gly Arg Leu Phe Thr Ser Asn Thr Thr Ala Pro
210                 215                 220

Gly Pro Asp Met Asp Ser Ala Leu Ser Phe Phe Arg Asp His Arg Tyr
225                 230                 235                 240

Pro Lys Asp Phe His Arg Ala Pro Val Pro Ser Gly Ala Arg Gly Leu
                245                 250                 255

Asp Val Val Ala Ala Ala Tyr Pro Ile Gln Pro Gly Tyr Asn Ala Asp
            260                 265                 270

Gly Lys Val Asn Asn Tyr Val Leu Asp Pro Thr Ser Ala Asp Phe Thr
        275                 280                 285
```

```
Lys Phe Cys Leu Leu Tyr Glu Asn Phe Val Leu Lys Thr Val Lys Gly
    290                 295                 300

Leu Tyr Pro Asn Pro Lys Gly Phe Leu Arg Lys Ala Leu Glu Thr Asn
305                 310                 315                 320

Leu Glu Tyr Phe Tyr Gln Ser Phe Pro Gly Ser Gly Gly Cys Pro Gln
                325                 330                 335

Val Phe Pro Trp Gly Lys Ser Asp
                340

<210> SEQ ID NO 3
<211> LENGTH: 351
<212> TYPE: PRT
<213> ORGANISM: Coprinopsis cinerea

<400> SEQUENCE: 3

Met Val Ser Cys Lys Leu Pro Leu Pro Leu Thr Leu Ala Ile Ala
1               5                   10                  15

Leu Ala Asn Val Asn Ala Phe Pro Ala Tyr Gln Ser Leu Gly Gly Leu
            20                  25                  30

Ser Lys Arg Gln Leu Glu Thr Ile Ile Pro Gly Leu Pro Val Val Asn
        35                  40                  45

Pro Gly Pro Pro Gly Pro Leu Ala Asp Ser Thr Leu Lys Leu Val
    50                  55                  60

Asn Asp Ala Ala His Pro Tyr Gln Ala Pro Arg Pro His Leu Asp His
65                  70                  75                  80

Arg Gly Pro Cys Pro Gly Leu Asn Thr Leu Ala Asn His Gly Tyr Leu
                85                  90                  95

Pro Arg Ser Gly Ile Ala Thr Pro Ala Gln Ile Val Gln Ala Val Met
            100                 105                 110

Glu Gly Phe Asn Met Glu Asn Thr Phe Ala Lys Phe Val Thr Tyr Ala
            115                 120                 125

Ala Phe Leu Val Asp Gly Asn Pro Ile Thr Asn Leu Met Ser Ile Gly
        130                 135                 140

Gly Lys Thr Trp Arg Thr Gly Ile Ile Glu Pro Pro Pro Ala Ile
145                 150                 155                 160

Val Gly Gly Leu Asn Thr His Ala Val Phe Glu Gly Asp Thr Ser Met
                165                 170                 175

Thr Arg Gly Asp Phe His Phe Gly Asp Asn His Ser Phe Asn Gln Thr
            180                 185                 190

Leu Phe Asp Gln Phe Val Glu Tyr Ser Asn Ile His Gly Gly Gly Phe
        195                 200                 205

Tyr Asn Leu Thr Ala Ala Thr Glu Leu Arg Tyr Gln Arg Ile Gln Gln
    210                 215                 220

Ser Ile Ala Thr Asn Pro Glu Met Ser Phe Val Ser Pro Arg Trp Phe
225                 230                 235                 240

Thr Ala Ile Leu Leu Gln Asp Glu Lys Phe Pro Asp Asp Phe His Arg
                245                 250                 255

Ala Pro Gly Pro Phe Ser Phe Glu Gly Leu Gly Tyr Leu Val Thr Arg
            260                 265                 270

Arg Pro Met Pro Pro Gly Arg Asn Val Gly Val Asp Asn Tyr Val
        275                 280                 285

Pro Asp Pro Asn Ser Ala Asp Phe Asn Ser Phe Cys Lys Met Tyr Glu
    290                 295                 300

Asp Phe Val Asn Asp Ile Val Val Ala Leu Tyr Pro Asn Pro Thr Gly
305                 310                 315                 320
```

```
Leu Leu Arg Arg Asn Leu Ile Lys Asn Leu Glu Tyr Phe Trp Thr Gly
            325                 330                 335

Met Phe Asp Pro Ala Cys Thr Glu Val Lys Pro Tyr Gly Thr Leu
            340                 345                 350

<210> SEQ ID NO 4
<211> LENGTH: 243
<212> TYPE: PRT
<213> ORGANISM: Aspergillus niger

<400> SEQUENCE: 4

Leu Ala Thr Gly Ser Thr Lys Leu Leu Pro Trp Ser Pro Gly His
1               5                   10                  15

Gly Asp Val Arg Gly Pro Cys Pro Met Leu Asn Thr Leu Ala Asn His
            20                  25                  30

Gly Leu Leu Pro His Asn Gly Lys Asp Ile Ser Gln Glu Val Ile Thr
            35                  40                  45

Glu Val Leu Asn Asn Thr Leu Asn Leu Ala Asp Gly Leu Ser Ala Phe
50                  55                  60

Leu Phe Glu Glu Ala Met Thr Thr Val Glu Asp Pro Lys Ala Thr Thr
65                  70                  75                  80

Phe Ser Leu Ser Asp Leu Asn Cys Pro Gly Ile Leu Glu His Asp Gly
            85                  90                  95

Ser Leu Ser Arg Gln Asp Thr Tyr Phe Gly Asn Asn His Glu Phe Asn
            100                 105                 110

Gln Thr Ile Phe Asp Gln Thr Lys Ser Tyr Trp Thr Thr Pro Leu Ile
            115                 120                 125

Asp Met Tyr Gln Ala Ala Glu Ala His Glu Ala Arg Leu Asn Thr Ser
            130                 135                 140

Lys Ala Thr Asn Pro Thr Phe Asn Leu Ser Glu Thr Gly Leu Thr Phe
145                 150                 155                 160

Ser Phe Gly Glu Thr Ala Ala Tyr Met Ile Val Phe Glu Asp Thr Asn
            165                 170                 175

Leu Gly Tyr Ala Asn Arg Ser Trp Val Glu Tyr Phe Phe Glu Asn Glu
            180                 185                 190

Arg Leu Pro Gln Glu Leu Gly Trp Thr Lys Arg Pro Phe Ile Thr Thr
            195                 200                 205

Gly Gln Val Leu Val Asp Met Thr Thr Trp Val Ile Asn Ser Thr Ile
            210                 215                 220

Gly Val Thr Pro Glu Glu Gln Ala Glu Met Gln Asp Phe Gly Lys Lys
225                 230                 235                 240

Ile Thr Gly

<210> SEQ ID NO 5
<211> LENGTH: 247
<212> TYPE: PRT
<213> ORGANISM: Aspergillus niger

<400> SEQUENCE: 5

Phe Pro Gln Gln Gly Ala Pro His Pro Leu Pro Trp Ser Pro Pro Gly
1               5                   10                  15

Pro Asn Asp Val Arg Ala Pro Cys Pro Met Leu Asn Thr Leu Ala Asn
            20                  25                  30

His Gly Tyr Leu Pro His Asn Gly Lys Asp Ile Thr Glu Arg His Thr
            35                  40                  45
```

```
Ile Asn Ala Leu Tyr Asn Ala Leu Gly Ile Glu Glu Leu Ala Ile
 50                  55                  60

Tyr Leu His Gln Glu Ala Val Thr Thr Asn Pro Ala Pro Asn Ala Thr
 65                  70                  75                  80

Thr Phe Ser Leu Asn Asp Leu Ser Arg His Asp Ile Leu Glu His Asp
                 85                  90                  95

Ala Ser Leu Ser Arg Gln Asp Ala Tyr Phe Gly Asp Asn His Asp Phe
            100                 105                 110

Asn Gln Thr Ile Phe Asp Glu Thr Arg Ser Tyr Trp Thr Ser Pro Ile
        115                 120                 125

Ile Asp Val Lys Gln Ala Ala Val Ser Arg Gln Ala Arg Val Asn Thr
130                 135                 140

Ser Met Ala Thr Asn Pro Asn Tyr Thr Met Ser Glu Leu Gly Asp Ser
145                 150                 155                 160

Phe Ser Tyr Gly Glu Thr Ala Ala Tyr Ile Ile Val Leu Gly Asp Lys
                165                 170                 175

Glu Lys Gly Leu Val Asn Arg Ser Arg Val Glu Tyr Leu Phe Glu Asn
            180                 185                 190

Glu Arg Leu Pro Leu Asp Leu Gly Trp Ser Arg Ala Lys Glu Asn Ile
        195                 200                 205

Thr Phe Asp Asp Leu Ser Thr Met Leu Gln Arg Ile Ile Asn Ala Thr
210                 215                 220

Gly Gly Glu Ser Glu Phe Asp Arg Glu Leu Ala Lys Arg Gly Gly Val
225                 230                 235                 240

His Val Gly Ser Trp Arg Gly
                245

<210> SEQ ID NO 6
<211> LENGTH: 259
<212> TYPE: PRT
<213> ORGANISM: Poronia punctata

<400> SEQUENCE: 6

Lys Ala Ala Cys Pro Tyr Gly Tyr Gly Glu Phe Gln Pro Glu Gln Thr
1               5                   10                  15

Ser Asp Ala Arg Gly Pro Cys Pro Val Leu Asn Thr Leu Ala Asn His
            20                  25                  30

Gly Tyr Leu Pro Arg Asp Gly Arg His Ile Asp Glu Asn Arg Thr Leu
        35                  40                  45

Thr Ala Leu His Asp Ala Leu Asn Leu Asp Ile Asp Phe Gly Lys Phe
 50                  55                  60

Leu Phe Thr Ala Gly Arg Leu Ser Asn Pro Lys Ala Asn Ser Thr Trp
 65                  70                  75                  80

Phe Asp Leu Asp His Leu Ser Arg His Gly Ile Phe Glu His Asp Gly
                 85                  90                  95

Ser Leu Ser Arg Gln Asp His His Phe Gly Glu Trp Ser Arg Phe Asn
            100                 105                 110

Gln Thr Val Trp Asn Trp Thr Leu Glu Tyr Leu Pro Asp Asp Met Leu
        115                 120                 125

Asp Val Gln Thr Val Ala Asn Ala Arg Ala Gln Arg Met Thr Arg Ser
130                 135                 140

Asn Leu Thr Asn Pro Asp Phe Ala Leu Ser Tyr Leu Gly Tyr Leu Phe
145                 150                 155                 160

Ser Val Gly Glu Ala Ala Ala Val Leu Ser Ile Leu Gly Asp Lys Lys
                165                 170                 175
```

```
Thr Gln Thr Cys Pro Lys Ala Phe Ala Asp Tyr Ile Phe Val Asn Glu
            180                 185                 190
Arg Leu Pro Tyr Glu Leu Gly Trp Lys Lys Gln Asp Ala Ser Ile Ser
        195                 200                 205
Phe Asp Asp Leu Val Glu Thr Phe Glu Asp Leu Glu Arg His Thr Ser
    210                 215                 220
Phe Pro Phe Pro Pro Leu Asp Asn Ser Thr Asp Ile Phe Asp Gln
225                 230                 235                 240
Leu Val Glu Gly Gly Gln Ser Lys Lys Lys Arg Cys Ser Ala His Ile
                245                 250                 255
Gly Cys Phe

<210> SEQ ID NO 7
<211> LENGTH: 259
<212> TYPE: PRT
<213> ORGANISM: Chaetomium virescens

<400> SEQUENCE: 7

Glu Leu Asp Phe Ser Lys Trp Lys Thr Arg Gln Pro Gly Glu Phe Arg
1               5                   10                  15
Ala Pro Cys Pro Ala Met Asn Ser Leu Ala Asn His Gly Phe Ile Pro
            20                  25                  30
Arg Asp Gly Arg Asn Ile Thr Val Ala Met Leu Val Pro Val Leu Gln
        35                  40                  45
Glu Val Phe His Leu Ser Pro Glu Leu Ala Gln Thr Ile Ser Thr Leu
    50                  55                  60
Gly Leu Phe Thr Ala Gln Asp Pro Ser Lys Gly Val Phe Thr Leu Asp
65                  70                  75                  80
Asp Leu Asn Arg His Asn Leu Phe Glu His Asp Ala Ser Leu Ser Arg
                85                  90                  95
Glu Asp Tyr Tyr Phe His Lys Asp Ala Ser Thr Phe Arg Pro Glu Val
            100                 105                 110
Phe Lys Lys Phe Met Ser His Phe Lys Gly Lys Glu Tyr Val Thr Leu
        115                 120                 125
Glu Asp Ala Ala Ser Ala Arg Tyr Ala Met Val Gln Glu Ser Arg Lys
    130                 135                 140
Lys Asn Pro Thr Phe Thr Tyr Thr Val Gln Gln Arg Ile Thr Ser Tyr
145                 150                 155                 160
Gly Glu Thr Ile Lys Tyr Phe Arg Thr Ile Val Glu Pro Ala Thr Gly
                165                 170                 175
Lys Cys Pro Val Ala Trp Ile Lys Ile Leu Phe Glu Gln Glu Arg Leu
            180                 185                 190
Pro Tyr Asn Glu Gly Trp Arg Pro Lys Ala Glu Leu Ser Gly Phe
        195                 200                 205
Ser Met Ala Ser Asp Val Leu Glu Leu Ala Leu Val Thr Pro Glu Lys
    210                 215                 220
Leu Ile Asp Lys Pro Cys Glu Gly Lys Gln Cys Pro Gln Ala Arg Gly
225                 230                 235                 240
Ile His Gly Tyr Phe Gly Met Leu Leu Pro Ile Thr Ala Gln Glu Leu
                245                 250                 255
Ala Val Lys
```

```
<210> SEQ ID NO 8
<211> LENGTH: 261
<212> TYPE: PRT
<213> ORGANISM: Humicola insolens

<400> SEQUENCE: 8

Gly Phe His Asp Trp Glu Pro Pro Gly Asn Asp Val Arg Ala Pro
1               5                   10                  15

Cys Pro Met Leu Asn Thr Leu Ala Asn His Gly Phe Leu Pro His His
            20                  25                  30

Gly Arg Asp Leu Thr Arg Lys Gln Val Val Asp Gly Leu Tyr Asn Gly
            35                  40                  45

Leu Asn Ile Asn Lys Thr Ala Ala Ser Thr Leu Phe Asp Phe Ala Leu
        50                  55                  60

Met Thr Ser Pro Lys Pro Asn Ala Thr Thr Phe Ser Leu Asp Asp Leu
65                  70                  75                  80

Gly Arg His Asn Ile Leu Glu His Asp Ala Ser Leu Ser Arg Thr Asp
                85                  90                  95

Ala Tyr Phe Gly Asp Val Leu Ala Phe Asn Lys Thr Ile Phe Glu Glu
            100                 105                 110

Thr Lys Arg His Trp Gly Lys Ser Pro Ile Leu Asp Val Thr Ala Ala
            115                 120                 125

Ala Arg Ala Arg Leu Gly Arg Ile Gln Thr Ser Lys Ala Thr Asn Pro
        130                 135                 140

Glu Tyr Phe Met Ser Glu Leu Gly Asn Ile Phe Thr Tyr Gly Glu Ser
145                 150                 155                 160

Val Ala Tyr Ile Met Leu Ile Gly Asp Ala Lys Thr Gly Arg Ala Asn
                165                 170                 175

Arg Arg Trp Val Glu Tyr Trp Phe Glu Asn Glu Arg Leu Pro Thr His
            180                 185                 190

Leu Gly Trp Arg Arg Pro Ser Lys Glu Leu Thr Ser Asp Val Leu Asp
        195                 200                 205

Thr Tyr Ile Ser Leu Ile Gln Asn Ile Thr Leu Thr Leu Pro Gly Gly
    210                 215                 220

Thr Asp Pro Val Lys Arg Arg Ala Ala Ser His Phe Val Phe Pro Phe
225                 230                 235                 240

Gly Gln Gly Leu Gly Gly Pro Ala Gly Val Ala Leu Met Leu Ile Ser
                245                 250                 255

Val Val Ala Tyr Gly
            260

<210> SEQ ID NO 9
<211> LENGTH: 242
<212> TYPE: PRT
<213> ORGANISM: Chaetomium globosum

<400> SEQUENCE: 9

Gly Phe Asp Thr Trp Ala Pro Pro Gly Pro Tyr Asp Val Arg Gly Pro
1               5                   10                  15

Cys Pro Met Leu Asn Thr Leu Thr Asn His Gly Phe Phe Pro His Asp
            20                  25                  30

Gly Gln Asp Ile Asp Arg Glu Thr Thr Glu Asn Ala Leu Phe Asp Ala
            35                  40                  45

Leu His Val Asn Lys Thr Leu Ala Ser Phe Leu Phe Asp Phe Ala Leu
        50                  55                  60
```

```
Thr Thr Asn Pro Ile Ala Asn Ser Thr Thr Phe Ser Leu Asn Asp Leu
 65                  70                  75                  80

Gly Asn His Asn Val Leu Glu His Asp Ala Ser Leu Ser Arg Ala Asp
                 85                  90                  95

Ala Tyr His Gly Ser Val Leu Ala Phe Asn His Thr Ile Phe Glu Glu
            100                 105                 110

Thr Lys Ser Tyr Trp Thr Asp Glu Thr Val Thr Leu Lys Met Ala Ala
        115                 120                 125

Asp Ala Arg Tyr Tyr Arg Ile Lys Ser Ser Gln Ala Thr Asn Pro Thr
130                 135                 140

Tyr Gln Met Ser Glu Leu Gly Asp Ala Phe Thr Tyr Gly Glu Ser Ala
145                 150                 155                 160

Ala Tyr Val Val Leu Phe Gly Asp Lys Glu Ser Gln Thr Val Pro Arg
                165                 170                 175

Ser Trp Val Glu Trp Leu Phe Glu Lys Glu Gln Leu Pro Gln His Leu
            180                 185                 190

Gly Trp Lys Arg Pro Ala Thr Ser Phe Glu Leu Asn Asp Leu Asp Lys
        195                 200                 205

Phe Met Ala Leu Ile Gln Asn Tyr Thr Gln Glu Ile Glu Glu Pro Ser
210                 215                 220

Cys Glu Ser Arg Lys Gln Arg Arg Lys Pro Arg Gly Pro Ser His Phe
225                 230                 235                 240

Gly Phe

<210> SEQ ID NO 10
<211> LENGTH: 243
<212> TYPE: PRT
<213> ORGANISM: Chaetomium globosum

<400> SEQUENCE: 10

Gly Phe Asp Thr Trp Ala Pro Pro Gly Pro Tyr Asp Val Arg Ala Pro
1               5                   10                  15

Cys Pro Met Leu Asn Thr Leu Ala Asn His Gly Phe Leu Pro His Asp
                20                  25                  30

Gly His Glu Ile Thr Arg Glu Gln Thr Glu Asn Ala Leu Phe Asp Ala
            35                  40                  45

Leu His Ile Asp Lys Met Leu Gly Ser Ser Leu Phe Asp Phe Ala Met
        50                  55                  60

Thr Thr Asn Pro Val Ala Asn Ser Thr Thr Phe Ser Leu Asn Asp Leu
 65                  70                  75                  80

Gly Asn His Asn Val Leu Glu His Asp Ala Ser Leu Ser Arg Ser Asp
                 85                  90                  95

Ala Tyr Phe Gly Asn Thr Leu Thr Phe Asn Gln Thr Val Phe Asp Glu
            100                 105                 110

Thr Lys Ser Tyr Trp Thr Asp Glu Thr Val Thr Ile Glu Met Ala Ser
        115                 120                 125

Asn Ala Arg Leu Ala Arg Ile Lys Thr Ser Asn Ala Thr Asn Pro Thr
130                 135                 140

Tyr Ser Met Ser Glu Leu Gly Asn Gly Phe Thr Lys Gly Glu Ser Ala
145                 150                 155                 160

Ala Tyr Val Val Ile Phe Gly Asp Lys Ile Ser Gly Thr Val Pro Arg
                165                 170                 175

Ala Trp Val Glu Trp Leu Phe Glu His Glu Gln Leu Pro Gln His Leu
            180                 185                 190
```

Gly Trp Lys Arg Pro Thr Glu Leu Phe Arg Asp Gly Asp Leu Asp Lys
            195                 200                 205

Tyr Met Asp Ala Met Gln Asn Val Ile Val Gly Glu Thr Pro Gly Cys
        210                 215                 220

Pro Ala Gly Lys Gln Gln Gln Arg Lys Gly Arg Arg Thr Pro Ser His
225                 230                 235                 240

Phe Gly Trp

<210> SEQ ID NO 11
<211> LENGTH: 276
<212> TYPE: PRT
<213> ORGANISM: Sclerotinia sclerotiorum

<400> SEQUENCE: 11

Met Lys Leu Asn Phe Leu Ser Thr Thr Leu Ala Leu Gly Leu Val Ser
1               5                   10                  15

Ala Arg Ala His Tyr Gln Gln Gln Ile Ile Ala Asn Asp Thr Glu Gly
            20                  25                  30

Glu Trp Ile Ala Pro Ser Ala Thr Asp Tyr Arg Gly Pro Cys Pro Met
        35                  40                  45

Leu Asn Thr Leu Ala Asn His Gly Phe Leu Pro Arg Asp Gly Arg Asn
    50                  55                  60

Leu Thr Glu His Asn Val Val Lys Gly Leu Asn His Gly Leu Asn Phe
65                  70                  75                  80

Asn Lys Ser Leu Gly Ser Ile Met Phe Gln His Ala Val Pro Ala Ser
                85                  90                  95

Pro Ala Tyr Pro Asn Thr Thr Phe Phe Thr Leu Asp Asp Leu Asn Arg
            100                 105                 110

His Asn Val Leu Glu His Asp Ala Ser Ile Ser Arg Ser Asp Ala Tyr
            115                 120                 125

Phe Gly Asn Asn His Ile Phe Asn Gln Thr Ile Phe Asp Thr Thr Lys
    130                 135                 140

Met Tyr Trp Pro Ser Glu Thr Leu Thr Ala Gln His Leu Ile Asp Gly
145                 150                 155                 160

Lys Ile Phe Arg Gln Ile Val Ser Arg Thr Thr Asn Pro Asn Tyr Thr
                165                 170                 175

Phe Thr Ser Thr Thr Gln Ala Phe Ser Leu Gly Glu Met Ala Ala Pro
            180                 185                 190

Ile Val Ala Phe Gly Asp Lys Asn Ala Leu Thr Ala Asn Arg Thr Leu
    195                 200                 205

Val Glu Ser Trp Ile Glu Asn Glu Arg Leu Pro Thr Glu Leu Gly Trp
210                 215                 220

Ser Lys Pro Glu Glu Val Ser Leu Gly Asp Ile Leu Tyr Val Thr
225                 230                 235                 240

Gly Ala Leu Ala Asn Leu Thr Ser Leu Leu Ser Asp Val Val Ile Thr
            245                 250                 255

Pro Arg Gly Glu Ser Ala Gly Ala His Ala Lys Arg Met Gly His Trp
            260                 265                 270

Gly Val Ser Met
        275

<210> SEQ ID NO 12
<211> LENGTH: 259
<212> TYPE: PRT
<213> ORGANISM: Aspergillus carbonarius

<400> SEQUENCE: 12

Met Lys Ser Thr Ile Leu Leu Ile Thr Thr Ser Leu Ser Gln Ala Leu
1               5                   10                  15

Ala Gln Val Ser Ser His Pro Phe Pro Trp Ser Ala Pro Gly Pro Asn
            20                  25                  30

Asp Val Arg Gly Pro Cys Pro Met Leu Asn Thr Leu Ala Asn His Gly
        35                  40                  45

Phe Leu Pro His Asp Gly Lys Asp Ile Thr Glu Asp Arg Ile Val Met
    50                  55                  60

Val Leu Asn Asn Ser Leu Asn Leu Asp Glu Glu Leu Ser Gln Phe Leu
65                  70                  75                  80

Phe Lys Glu Ala Leu Thr Thr Asn Pro Asp Pro Asn Ala Thr Thr Phe
                85                  90                  95

Ser Leu Asn Asp Leu Ser Arg His Asn Ile Leu Glu His Asp Ala Ser
            100                 105                 110

Leu Ser Arg Gln Asp Tyr Tyr Phe Gly Asp Asn His Asp Phe Asn Gln
        115                 120                 125

Thr Val Phe Asn Glu Thr Arg Ser Tyr Trp Thr Ala Pro Leu Ile Asp
    130                 135                 140

Phe Asn Ala Ala Ala Gln Ala Arg Leu Ala Arg Val Asn Thr Ser Met
145                 150                 155                 160

Ala Thr Asn Pro Thr Tyr Thr Glu Ser Glu Thr Gly Leu Ala Phe Ser
                165                 170                 175

Tyr Gly Glu Ser Ala Ala Tyr Met Ile Val Phe Ala Glu Gly Ser Glu
            180                 185                 190

Thr Ala Asn Arg Ser Trp Val Glu Tyr Phe Glu His Glu Arg Leu
        195                 200                 205

Pro Gln Gln Leu Gly Trp Thr Lys Pro Gln Glu Ser Ile Ser Ser Ser
    210                 215                 220

Val Leu Ile Asp Thr Val Thr Gly Ile Ala Asn Ala Ser Asn Ala Ser
225                 230                 235                 240

Ser Leu Val Val Ala Glu Leu Leu Asp Phe Val Ala Leu His Met Gly
                245                 250                 255

Arg Leu Pro

<210> SEQ ID NO 13
<211> LENGTH: 247
<212> TYPE: PRT
<213> ORGANISM: Penicillium chrysogenum

<400> SEQUENCE: 13

Ser Pro Gly Ala Gly Trp Lys His Ala Leu Gln Trp Lys Pro Ala Gly
1               5                   10                  15

Glu Ser Asp Tyr Arg Gly Pro Cys Pro Met Met Asn Thr Leu Ala Asn
            20                  25                  30

His Gly Phe Leu Pro His Asp Gly Arg Asn Ile Thr Arg Pro Asn Leu
        35                  40                  45

Val Asp Ala Leu Gly Gln Ala Leu Asn Phe Asn Gly Leu Ala Ser
    50                  55                  60

Leu Met Phe Asp Met Gly Val Val Ala Asn Pro Glu Pro Asn Ala Thr
65                  70                  75                  80

Val Phe Thr Leu Asp Asp Leu Asn Arg His Asn Val Leu Glu His Asp
                85                  90                  95

```
Ala Ser Leu Ser Arg Ser Asp Ala Phe Phe Gly Ser Asn His Val Phe
            100                 105                 110

Asn Glu Thr Ile Phe Glu Thr Lys Ala Tyr Trp Thr Gly Pro Ile
        115                 120                 125

Leu Asp Ala Glu Met Leu Ala Asn Ser Lys Val Ala Arg Gln Ile Asn
    130                 135                 140

Ser Lys Ala His Asn Pro Thr Tyr Thr Phe Thr Ala Asn Thr Glu Gln
145                 150                 155                 160

Phe Ser Leu Gly Glu Val Ala Ala Pro Ile Ile Ala Phe Gly Asp Ile
                165                 170                 175

Gln Ala Gly Thr Val Asn Arg Ser Leu Val Glu Tyr Phe Phe Glu Asn
            180                 185                 190

Glu Arg Leu Pro Thr Asp Leu Gly Trp Lys Arg Pro Ala Lys Val Thr
        195                 200                 205

Ser Leu Gln Asp Ile Leu Ser Val Thr Gln Met Ile Lys Lys Ala Ser
    210                 215                 220

Arg Leu Ile Thr Pro Ser Glu Ser Ser Pro Ala Arg His Gln Gly Ser
225                 230                 235                 240

Ser Gln Val Asn Leu His Gly
                245

<210> SEQ ID NO 14
<211> LENGTH: 244
<212> TYPE: PRT
<213> ORGANISM: Daldinia caldariorum

<400> SEQUENCE: 14

Ala Pro Trp Lys Ala Pro Gly Pro Asp Asp Val Arg Gly Pro Cys Pro
1               5                   10                  15

Met Leu Asn Thr Leu Ala Asn His Gly Phe Leu Pro His Asp Gly Lys
            20                  25                  30

Asn Ile Asp Val Asn Thr Thr Val Asn Ala Leu Ser Ser Ala Leu Asn
        35                  40                  45

Leu Asp Asp Glu Leu Ser Arg Asp Leu His Thr Phe Ala Val Thr Thr
    50                  55                  60

Asn Pro Gln Pro Asn Ala Thr Trp Phe Ser Leu Asn His Leu Ser Arg
65                  70                  75                  80

His Asn Val Leu Glu His Asp Ala Ser Leu Ser Arg Gln Asp Ala Tyr
                85                  90                  95

Phe Gly Pro Pro Asp Val Phe Asn Ala Ala Val Phe Asn Glu Thr Lys
            100                 105                 110

Ala Tyr Trp Thr Gly Asp Ile Ile Asn Phe Gln Met Ala Ala Asn Ala
        115                 120                 125

Leu Thr Ala Arg Leu Met Thr Ser Asn Leu Thr Asn Pro Glu Phe Ser
    130                 135                 140

Met Ser Gln Leu Gly Arg Gly Phe Gly Leu Gly Glu Thr Val Ala Tyr
145                 150                 155                 160

Val Thr Ile Leu Gly Ser Lys Glu Thr Arg Thr Val Pro Lys Ala Phe
                165                 170                 175

Val Glu Tyr Leu Phe Glu Asn Glu Arg Leu Pro Tyr Glu Leu Gly Phe
            180                 185                 190

Lys Lys Met Lys Ser Ala Leu Thr Glu Asp Glu Leu Thr Thr Met Met
        195                 200                 205

Gly Glu Ile Tyr Ser Leu Gln His Leu Pro Glu Ser Phe Thr Lys Pro
    210                 215                 220
```

```
Phe Ala Lys Arg Ser Glu Ala Pro Phe Glu Arg Ala Glu Lys Arg
225                 230                 235                 240
Cys Pro Phe His

<210> SEQ ID NO 15
<211> LENGTH: 244
<212> TYPE: PRT
<213> ORGANISM: Myceliophthora fergusii

<400> SEQUENCE: 15

Gly Phe Asp Thr Trp Ser Pro Pro Gly Pro Tyr Asp Val Arg Ala Pro
1               5                   10                  15

Cys Pro Met Leu Asn Thr Leu Ala Asn His Gly Phe Leu Pro His Asp
            20                  25                  30

Gly Lys Asp Ile Thr Arg Glu Gln Thr Glu Asn Ala Leu Phe Glu Ala
        35                  40                  45

Leu His Ile Asn Lys Thr Leu Gly Ser Phe Leu Phe Asp Phe Ala Leu
50                  55                  60

Thr Thr Asn Pro Arg Asn Thr Ser Thr Phe Ser Leu Asn Asp Leu Gly
65                  70                  75                  80

Asn His Asn Ile Leu Glu His Asp Ala Ser Leu Ser Arg Ala Asp Ala
                85                  90                  95

Tyr Phe Gly Asn Val Leu Gln Phe Asn Gln Thr Val Phe Asp Glu Thr
            100                 105                 110

Lys Thr Tyr Trp Asp Gly Asp Val Ile Asp Leu Arg Met Ala Ala Arg
        115                 120                 125

Ala Arg Leu Gly Arg Ile Lys Thr Ser Gln Ala Thr Asn Pro Thr Tyr
130                 135                 140

Ser Met Ser Glu Leu Gly Asp Ala Phe Thr Tyr Gly Glu Ser Ala Ala
145                 150                 155                 160

Tyr Val Val Leu Gly Asp Lys Glu Ser Arg Thr Ala Lys Arg Ser
            165                 170                 175

Trp Val Glu Trp Phe Phe Glu His Glu Gln Leu Pro Gln His Leu Gly
            180                 185                 190

Trp Lys Arg Pro Ala Ser Ser Leu Glu Glu Asp Leu Phe Thr Ile
        195                 200                 205

Met Asp Glu Ile Arg Gln Tyr Thr Ser Glu Leu Glu Gly Ser Thr Ser
210                 215                 220

Ser Ser Asp Ala Gln Thr Ser Arg Arg Gln Leu Pro Arg Arg Arg Thr
225                 230                 235                 240

His Phe Gly Phe

<210> SEQ ID NO 16
<211> LENGTH: 244
<212> TYPE: PRT
<213> ORGANISM: Myceliophthora hinnulea

<400> SEQUENCE: 16

Gly Phe Asp Thr Trp Ser Pro Pro Gly Pro Tyr Asp Val Arg Ala Pro
1               5                   10                  15

Cys Pro Met Leu Asn Thr Leu Ala Asn His Gly Phe Leu Pro His Asp
            20                  25                  30

Gly Lys Asp Ile Thr Arg Glu Gln Thr Glu Asn Ala Leu Phe Asp Ala
        35                  40                  45

Leu Asn Ile Asn Lys Thr Leu Ala Ser Phe Leu Phe Asp Phe Ala Leu
50                  55                  60
```

```
Thr Thr Asn Pro Lys Asn Thr Ser Thr Phe Ser Leu Asn Asp Leu Gly
 65                  70                  75                  80

Asn His Asn Ile Leu Glu His Asp Ala Ser Leu Ser Arg Ala Asp Ala
                 85                  90                  95

Tyr Phe Gly Asn Val Leu Gln Phe Asn Gln Thr Val Phe Asp Glu Thr
            100                 105                 110

Lys Thr Tyr Trp Glu Gly Asp Thr Ile Asp Leu Arg Met Ala Ala Lys
        115                 120                 125

Ala Arg Leu Gly Arg Ile Lys Thr Ser Gln Ala Thr Asn Pro Thr Tyr
    130                 135                 140

Ser Met Ser Glu Leu Gly Asp Ala Phe Thr Tyr Gly Glu Ser Ala Ala
145                 150                 155                 160

Tyr Val Val Leu Gly Asp Lys Glu Ser Arg Thr Val Asn Arg Ser
                165                 170                 175

Trp Val Glu Trp Phe Phe Glu His Glu Gln Leu Pro Gln His Leu Gly
            180                 185                 190

Trp Lys Arg Pro Ala Val Ser Phe Glu Glu Asp Leu Asn Arg Phe
        195                 200                 205

Met Glu Glu Ile Glu Lys Tyr Thr Lys Gly Leu Glu Gly Ser Asn Ser
210                 215                 220

Thr Ser Gly Ser Gln Lys His Arg Arg Arg Leu Pro Arg Arg Arg Thr
225                 230                 235                 240

His Phe Gly Phe

<210> SEQ ID NO 17
<211> LENGTH: 249
<212> TYPE: PRT
<213> ORGANISM: Thielavia terrestris

<400> SEQUENCE: 17

Ser Pro Asp Trp Ser Ser Pro Glu Phe Trp Ser Trp His Pro Pro Ala
1               5                   10                  15

Pro Gly Asp Asp Arg Arg Gly Pro Cys Pro Met Leu Asn Thr Leu Ala
            20                  25                  30

Asn His Gly Phe Leu Pro His Asn Gly Arg Asn Ile Thr Lys Glu Ile
        35                  40                  45

Thr Val Asn Ala Leu Asn Ser Ala Leu Asn Val Asn Lys Thr Leu Gly
    50                  55                  60

Glu Leu Leu Phe Asn Phe Ala Val Thr Thr Asn Pro Gln Pro Asn Ala
65                  70                  75                  80

Thr Phe Phe Asp Leu Asp His Leu Ser Arg His Asn Ile Leu Glu His
                85                  90                  95

Asp Ala Ser Leu Ser Arg Ala Asp Tyr Tyr Phe Gly His Asp Asp His
            100                 105                 110

Thr Phe Asn Gln Thr Val Phe Asp Gln Thr Lys Ser Tyr Trp Lys Thr
        115                 120                 125

Pro Ile Ile Asp Val Gln Gln Ala Asn Ala Arg Leu Ala Arg Val
    130                 135                 140

Leu Thr Ser Asn Ala Thr Asn Pro Thr Phe Val Leu Ser Gln Ile Gly
145                 150                 155                 160

Glu Ala Phe Ser Phe Gly Glu Thr Ala Ala Tyr Ile Leu Ala Leu Gly
                165                 170                 175

Asp Arg Val Ser Gly Thr Val Pro Arg Gln Trp Val Glu Tyr Leu Phe
            180                 185                 190
```

```
Glu Asn Glu Arg Leu Pro Leu Glu Leu Gly Trp Arg Arg Ala Lys Glu
            195                 200                 205

Val Ile Ser Asn Ser Asp Leu Asp Gln Leu Thr Asn Arg Val Ile Asn
210                 215                 220

Ala Thr Gly Ala Leu Ala Asn Ile Thr Arg Lys Ile Lys Val Arg Asp
225                 230                 235                 240

Phe His Ala Gly Arg Phe Pro Gly Glu
            245

<210> SEQ ID NO 18
<211> LENGTH: 241
<212> TYPE: PRT
<213> ORGANISM: Thielavia hyrcaniae

<400> SEQUENCE: 18

Gly Phe Asp Thr Trp Ser Pro Gly Pro Tyr Asp Val Arg Ala Pro
1               5                   10                  15

Cys Pro Met Leu Asn Thr Leu Ala Asn His Gly Phe Leu Pro His Asp
                20                  25                  30

Gly Lys Asp Leu Thr Arg Asp Val Val Glu Asn Ala Leu Ser Asp Ala
            35                  40                  45

Leu Asn Ile Asn Lys Thr Leu Gly Ser Phe Leu Phe Asp Phe Ala Leu
50                  55                  60

Thr Thr Asn Pro Lys Pro Asn Ser Thr Thr Phe Ser Leu Asn Asp Leu
65                  70                  75                  80

Gly Asn His Asn Ile Leu Glu His Asp Ala Ser Leu Ser Arg Ser Asp
                85                  90                  95

Ala Tyr Phe Gly Asn Val Leu Val Phe Asn Gln Ser Val Phe Asp Glu
            100                 105                 110

Thr Lys Ser Tyr Phe Lys Gly Lys Thr Val Thr Leu Lys Gln Ala Ala
            115                 120                 125

Gln Ala Arg Leu Ala Arg Ile Lys Thr Ser Lys Ala Thr Asn Pro Thr
130                 135                 140

Tyr Ser Met Ser Gln Leu Gly Asp Ser Phe Thr Tyr Gly Glu Ser Ala
145                 150                 155                 160

Ala Tyr Val Val Val Leu Gly Gly Asp Lys Lys Ser Ala Thr Val Pro
                165                 170                 175

Arg Ser Trp Val Glu Trp Phe Phe Glu His Glu Gln Leu Pro Gln His
            180                 185                 190

Leu Gly Trp Lys Arg Pro Ala Glu Gln Phe Thr Gln Asp Asp Leu Asn
            195                 200                 205

Lys Phe Met Asp Glu Ile Ile Asn Ile Thr Lys Ala Ile Asp His Arg
210                 215                 220

Ser Val Asp Val Pro Glu Lys Thr Lys Arg Arg Ile Ser His Trp Gly
225                 230                 235                 240

Ala

<210> SEQ ID NO 19
<211> LENGTH: 237
<212> TYPE: PRT
<213> ORGANISM: Pestalotiopsis virgatula
```

```
<400> SEQUENCE: 19

Asp Phe Asp Thr Trp Ser Pro Gly Pro Asp Val Arg Ala Pro
1               5                   10                  15

Cys Pro Met Leu Asn Ser Leu Ala Asn His Gly Phe Pro His Asp
            20                  25                  30

Gly Lys Asp Ile Thr Glu Asp Val Thr Ile Ala Ala Leu Ala Asp Ala
            35                  40                  45

Leu Asn Val Asp Lys Ser Leu Ser Gln Phe Leu His Asp Lys Ala Val
50                  55                  60

Ser Thr Asn Pro Thr Pro Gly Ala Thr Thr Phe Ser Leu Ser Asp Leu
65                  70                  75                  80

Ser Asn His Asn Ile Leu Glu His Asp Ala Ser Leu Ser Arg Ala Asp
                85                  90                  95

Tyr Tyr Trp Gly Asp Asp His Thr Phe Asn Glu Thr Val Phe Asn Glu
                100                 105                 110

Thr Arg Ser Tyr Trp Thr Asp Glu Thr Val Thr Val Lys Met Ala Ala
            115                 120                 125

Asp Ala Arg Leu Ala Arg Val His Ser Ser Ile Ala Thr Asn Pro Ser
130                 135                 140

Tyr Ser Met Ser Asp Leu Gly Asn Glu Phe Ser Leu Gly Glu Thr Ala
145                 150                 155                 160

Ala Tyr Ile Ile Ala Leu Gly Asp Arg Asp Asp Ala Thr Val Gln Lys
                165                 170                 175

Ser Phe Val Glu Tyr Leu Phe Glu Asn Glu Arg Leu Pro Leu Glu Leu
            180                 185                 190

Gly Trp Ala Arg Pro Glu Glu Leu Ile Asp Leu Gly Asp Val Gln Asp
            195                 200                 205

Met Leu Phe Arg Val Ile Asp Ala Thr Asp Ser Asp Ala Ala Thr Met
210                 215                 220

Ala Lys Leu Arg Lys Arg Gly Gly Tyr His Ala Gly Leu
225                 230                 235

<210> SEQ ID NO 20
<211> LENGTH: 246
<212> TYPE: PRT
<213> ORGANISM: Pestalotiopsis virgatula

<400> SEQUENCE: 20

Asp Gly Cys Ser Asn Tyr Ser Val Pro Glu Trp His Pro Pro Thr Glu
1               5                   10                  15

Gly Asp Val Arg Gly Pro Cys Pro Met Leu Asn Thr Leu Ala Asn His
            20                  25                  30

Gly Tyr Leu Pro His Ser Gly Lys Asp Ile Asn Val Asn Lys Thr Ile
            35                  40                  45

Asp Ala Leu Gly Gln Ala Leu Asn Ile Asp Ala Glu Leu Ala Thr Phe
50                  55                  60

Leu His Ser Phe Ala Val Thr Thr Asn Pro Thr Pro Asn Ala Thr Ile
65                  70                  75                  80

Phe Ser Leu Asp Asn Leu Ser Arg His Asn Ile Leu Glu His Asp Gly
                85                  90                  95

Ser Leu Ser Arg Ala Asp Tyr Tyr Trp Thr Gly Asp Ala Thr Ser Phe
                100                 105                 110

Asn Gln Thr Val Phe Asp Glu Thr Arg Ser Tyr Trp Thr Thr Pro Ile
            115                 120                 125
```

```
Ile Asp Met Glu Gln Ala Ala Ala Ala Arg Val Ala Arg Met Gln Thr
    130                 135                 140
Ser Gln Ala Thr Asn Pro Asn Phe Thr Leu Ser Asp Leu Gly Ser Ala
145                 150                 155                 160
Phe Ser Ile Gly Glu Ser Ala Ala Tyr Ile Phe Ile Leu Gly Asp Arg
                165                 170                 175
Val Ser Gly Thr Val Glu Arg Ser Leu Val Glu Tyr Leu Phe Glu Asn
                180                 185                 190
Glu Arg Leu Pro Thr Ala Leu Gly Trp Lys Arg Ala Ala Glu Ser Ile
            195                 200                 205
Ser Glu Asp Asp Leu Ala Asp Ala Met Asp Arg Ile Val Asn Ala Thr
    210                 215                 220
Asn Thr Asn Thr Thr Ala Gly Thr Ser Lys Arg Gly Ile Asn Gly Arg
225                 230                 235                 240
Ala Arg Leu Pro Arg Leu
                245

<210> SEQ ID NO 21
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu or Ile

<400> SEQUENCE: 21

Glu His Asp Xaa Ser Xaa Ser Arg
1               5
```